United States Patent [19]

Newman et al.

[11] Patent Number: 5,045,479
[45] Date of Patent: Sep. 3, 1991

[54] CONTINUOUS FLOW COMPETETIVE ASSAY WITH REFERENCE SYSTEM

[75] Inventors: Arnold L. Newman, Kensington; William D. Stanbro, Columbia, both of Md.

[73] Assignee: The Johns Hopkins University, Baltimore, Md.

[21] Appl. No.: 215,106

[22] Filed: Jul. 5, 1988

[51] Int. Cl.⁵ .............................................. C12M 1/40
[52] U.S. Cl. .................... 436/518; 435/288; 435/291; 435/808; 436/52; 436/56; 436/172
[58] Field of Search .................. 435/288, 291, 808; 436/524, 523, 52, 56, 172, 518

[56] References Cited

U.S. PATENT DOCUMENTS

| | | | |
|---|---|---|---|
| 3,370,175 | 2/1968 | Jordan et al. | 250/217 |
| 4,067,959 | 1/1978 | Bolz | 424/23 |
| 4,092,408 | 5/1978 | Litt | 424/23 |
| 4,113,434 | 9/1978 | Tanaka et al. | 23/232 |
| 4,181,650 | 1/1980 | Maier, Jr. | 260/112.5 |
| 4,205,952 | 6/1980 | Cais | 23/230 |
| 4,222,743 | 9/1980 | Wang | 23/230 |
| 4,251,360 | 2/1981 | Goldie et al. | 424/1.5 |
| 4,254,084 | 3/1981 | Blum | 422/81 |
| 4,263,406 | 4/1981 | Bostick et al. | 435/291 |
| 4,357,420 | 11/1982 | Bostick et al. | 435/8 |
| 4,388,411 | 6/1983 | Lovelock | 436/149 |
| 4,493,793 | 1/1985 | Chu | 260/112 |
| 4,510,251 | 4/1985 | Kirkemo et al. | 436/536 |
| 4,526,871 | 7/1985 | Avrameas et al. | 436/504 |
| 4,652,520 | 3/1987 | Bauman | 435/34 |
| 4,865,984 | 9/1989 | Nemerson et al. | 435/288 |
| 4,895,809 | 1/1990 | Schlaback et al. | 436/518 |

*Primary Examiner*—David L. Lacey
*Assistant Examiner*—J. D. Waack
*Attorney, Agent, or Firm*—Robert E. Archibald; Mary Louise Beall

[57] ABSTRACT

The invention relates to a continuous flow competitive assay system for the detection and measurement of chemical and biochemical analytes. It is a time-based, continuous on-line measurement of analyte concentrations comprising three functional assemblies connected in series: a sampler, a reactor and a detector. Tagged immunochemical discharged from the reactor is detected in the detector which contains a model of system response with the tagged immunochemical and keeps track of the amount of tagged immunochemical lost during the course of the operation of the reactor.

26 Claims, 2 Drawing Sheets

CONTINUOUS FLOW COMPETETIVE ASSAY WITH REFERENCE SYSTEM

STATEMENT OF GOVERNMENT INTEREST

The Government has rights in this invention pursuant to Contract No. N00024-85-C-5301.

BACKGROUND OF THE INVENTION

The present invention relates to a continuous flow assay system for the measurement of chemical and biochemical analytes.

Analytical techniques using antigen/antibody or other biological affinity reactions have proved extremely useful in measuring minute quantities of substances. However, substantially all the techniques used to date only allow a static assay at a single point in time. While serial sampling is possible, this is often laborious or impractical. In these situations a continuous flow system would be a great utility.

U.S. Pat. No. 4,251,360 relates to an immunochemical antigen/antibody reaction for the detection and identification of either an antigen or an antibody. The method involves introducing successive mixtures of the sample with a set amount of one component of the reaction in tagged form and another component bound to a carrier into the reactant stream. Although the stream is continuous, the successive mixtures are separated by the insertion of an air segment into the liquid portion of the stream. The carrier is particulate.

U.S. Pat. No. 4,181,650 discloses a non-continuous competitive reaction for the detection and measurement of a ligand in a liquid sample. A tagged form of the ligand to be detected as well as an antibody having receptors is introduced into the fluid to be assayed. Any untagged ligand present in the fluid competes on an equal basis with the tagged ligand for the available binding or receptor sites on the antibody. The amount of untagged ligand is determined by measuring either the free tagged ligand or the tagged ligand/antibody complex. The tag is a chemiluminescent substance.

U.S. Pat. No. 4,067,959 also relates to a non-continuous competitive reaction for the quantitation of an antigen or antibody in a liquid sample. A first immunochemical, either antigen or antibody is immobilized on a small disk type solid support and the second immunochemical, specific to the first and tagged with a fluorescent compound, is bound to the first immunochemical. The immunochemical to be quantitated competes with the tagged second immunochemical for binding sites on the first immunochemical.

U.S. Pat. No. 4,205,952 relates to specific binding assays using labelled or tagged constituents. The particular tags are one or more metal atoms selected from various metalo-organic derivatives or metal coordination complexes. The following metals are disclosed: manganese, bismuth, silver, silicon, aluminum, zinc, gold, lead, cadmium, cobalt, iron, nickel, antimony, thallium, palladium, platinum and chromium.

U.S. Pat. No. 3,370,175 relates to a device to detect toxicants in gaseous or aerosol form. A culture of luminous organism is exposed to air which may contain a low concentration of toxicant. When a toxicant contacts the luminous culture, a rapid change in light output occurs which is detected by a photodetector. Although the culture can be exposed to air for a long period of time, this is a static reaction, not a continuous flow. Also, this is not a specific binding assay.

The following U.S. patents relate to the general subject of non-continuous specific binding assays: U.S. Pat. Nos. 4,092,408; 4,222,743; 4,254,084; 4,493,793; 4,510,251 and 4,526,871.

U.S. Pat. Nos. 4,113,434 and 4,388,411 relate to devices and methods for sampling gases from a fluid flow. U.S. Pat. No. 4,113,434 is a continuous sampling method.

OBJECTS OF THE INVENTION

The main object of the present invention is a continuous method to detect and measure analytes in a flow.

Another object is to detect and measure the presence of toxicants in a particular environment with the passage of time.

It is also an object of the present invention to provide a continuous competitive binding method and apparatus for the detection and measurement of analytes.

Another object of this invention is to provide a continuous method to detect and measure the presence of an analyte in a sample wherein detection and measurement is based on a computer model of the response of a known quantity of the same analyte as a function of time.

SUMMARY OF THE INVENTION

This invention relates to the continuous detection and measurement of chemical and biochemical analytes in a flow. It is a time-based, continuous on-line measurement of analyte concentrations.

Figure 1:
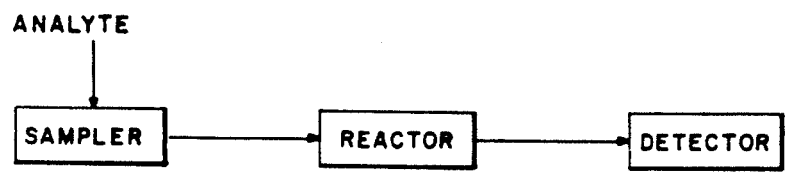
FIG. 1 is a block diagram of the Continuous Flow Assay System of the present invention.

The basic system comprises three functional assemblies connected in series as shown in FIG. 1: a sample collector assembly (sampler), a chemical reaction assembly (reactor), and a detection assembly (detector). This system is further supported by control electronics, signal conditioning, processing electronics, a reference system, and a flow pump.

The role of the sampler is to capture a sample to be assayed for an analyte and conduct it into the reactor.

The reactor contains a solid material having a large surface area. Conjugated or immobilized on the solid material is, for example, an immunochemical specific to the analyte to be detected. This first immunochemical is bound to a second immunochemical which is a tagged or labeled form of the same analyte.

The detector is connected to the reactor assembly and is used to detect tagged analyte leaving the reactor assembly.

In its simplest form the sampler is a tube that introduces the aqueous fluid to be analyzed into the reactor. In a medical application, this is an intravenous tube with a backflow stop valve, for example. Other configurations are determined by the physical state of the analyte: solid, liquid or gas.

The invention is based on a competitive type reaction involving specific binding partners. Either of the first and second immunochemicals may be an antigen or an antibody. However, one of the first and second immunochemicals must be the specific binding partner of the other. For example if the first or immobilized immunochemical is an antigen, the second or tagged immunochemical must be its specific antibody. In a like manner, if the first immunochemical is an antibody, the second is its specific antigen. One of the immunochemicals must be a tagged form of the analyte or an immobilized form of the analyte.

The analyte to be detected may be an antigen such as a chemical, a microorganism or a toxin, for example. The specific binding partner may be an antibody and, more particularly, a monoclonal antibody, for example.

The solid surface on which the first immunochemical is immobilized may be microspheres, a gel or the inner surface of the reactor. Sephadex or glass beads are particularly useful.

The tag or label is a substance not ordinarily present in the analyte or its environment. A variety of fluorescent compounds such as chelates of europium and terbium as well as radioactive elements are useful. A metal atom such as, for example, cesium, barium or lithium, is also an effective tag. For the metal atoms, mass spectrometer or atomic absorption techniques are used to detect the tag.

In operation, the sampler captures the sample, places it in an aqueous solution and delivers the solution into the reactor. Once in the reactor, any analyte present in the sample will compete with the tagged form of the analyte, the second immunochemical, for the available binding sites on the immobilized first immunochemical. Since this is a continuous flow system, unbound tagged analyte, replaced on the binding sites of the first immunochemical by analyte in the sample, is discharged from the reactor assembly and is measured by the detector. This measurement, adjusted by appropriate controls, is electronically processed to provide the concentration of the untagged analyte in the input sample.

The correlation of the amount of tagged analyte in the system output with the concentration of untagged analyte in the system input is complicated because binding relationship of the first immunochemical to the second immunochemical is actually a dynamic equilibrium. This means that in a static system, with no analyte present, the first and second immunochemicals are constantly dissociating and rebinding according to either of the present equations:

OR

Ab = Antibody
Ag = Antigen
TAb = Tagged Antibody
Tagged = Tagged Antigen

In the continuous flow system of the present invention, this would result in some of the tagged analyte constantly being swept into the detector even in the absence of untagged analyte in the input. Further, the amount of tagged analyte will be declining constantly as more and more analyte is lost. Moreover, when untagged analyte is present, the increasing amount of unbound tagged analyte will more effectively compete with untagged analyte for the unbound antibody and will cause a decrease in the amount of tagged analyte released for a given untagged analyte input.

These problems are resolved by using a microprocessor based system that contains a model of system response with the tagged immunochemical immunologically bound to its specific binding partner and without the presence of analyte. The system also tracks the amount of tagged immunochemical lost during operation of the reaction assembly. The final result is then reported using a suitable output device.

DESCRIPTION OF A PREFERRED EMBODIMENT

The sampler captures a sample to be assayed for a particular analyte, in this case the antigen cortisol, and places it in an aqueous solution that flows in to the reactor.

The reactor is an aqueous compartment and contains cortisol, the bound antigen, bound to the surface of glass beads. To bind the antigen, propyl amine groups are placed on the glass surface by reacting the glass with 3-aminopropyl(triethoxy)silane. Next the hemisuccinate derivative of the cortisol is formed by reacting the cortisol with succinic anhydride in pyridine. The cortisol hemisuccinate is then conjugated to the amino group attached to the surface of the bead using water soluble carbodiimide as a catalyst.

An anti-cortisol antibody prepared according to the method described by M.W. Sundberg ("Selective Binding of Metal Ions to Macro molecules Using Bifunctional Analogs of EDTA", *Journal of Medicinal Chemistry*, vol. 17, no. 12, 1974) or J.E. Kuo, et al ("Direct measurement of antigens in serum by Time-Resolved Fluoroimmunoassay", *Clinical Chemistry*, vol. 31, no. 1, 1985) and tagged with a terbium-EDTA chelate fluorescent material, is attached to the bound cortisol. As discussed above and as represented in equation (1), in the aqueous environment of the reactor the relationship of the bound antigen to the tagged antibody is a dynamic equilibrium wherein the tagged antibody is constantly dissociating and reassociating. As the aqueous solution flows through the reactor, any cortisol present in the aqueous sample competes with the bound cortisol for the tagged antibody. Since this is a continuous process, sample cortisol bound to tagged antibody as well as free tagged antibody is swept into the detector.

Figure 2:
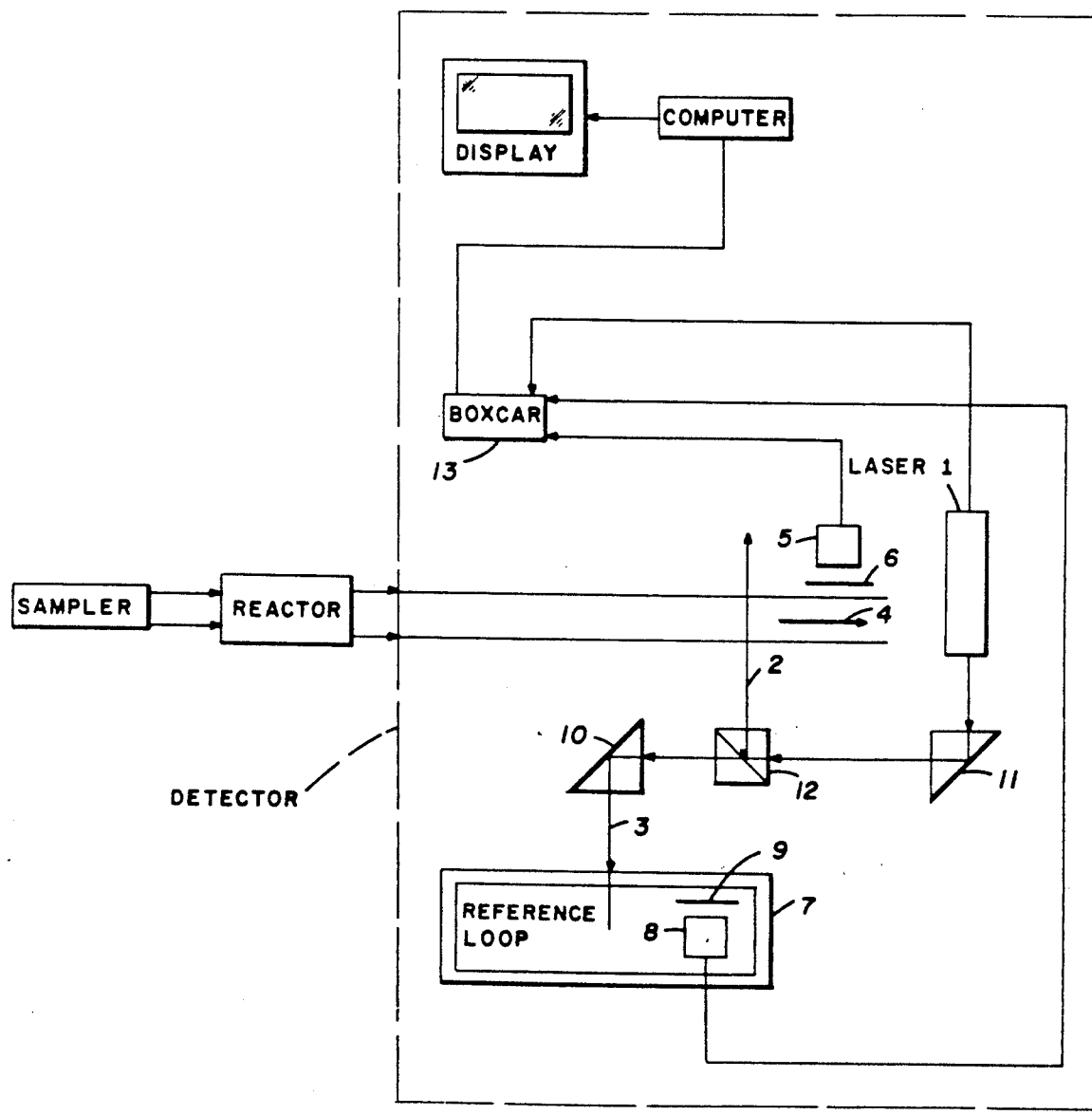
FIG. 2 is a block diagram of the system of the invention including means to detect a fluorescent tag.

As shown in the portion of FIG. 2 enclosed by the dash lines, the detector in this embodiment consists of a light source, which in this case is a nitrogen laser-emitting radiation at 337 nm. In the beam splitter 12, the laser beam is split into two parts 2 and 3 respectively. The first part 2 of the split beam is used in the sample detector system and passes through the exit stream 4 of the reaction chamber. At right angles to and slightly down stream from the laser beam is a light sensor, which in this case is a silicon photodiode 5 to detect emissions from the fluorophore tag excited by the laser. A filter 6 excluding light below 600 nm is placed in front of the photodiode to exclude any scattered laser light. The second part of the split laser beam 3 is used in a reference system consisting of a recirculating reference loop containing a known amount of immunochemical, in this case tagged antibody, and having a detector system identical to the sample system described above and including photodiode 8 as light sensor and filter 9. Numerals 10 and 11 represent mirrors. The reference system also measures emissions from excited tags and is a control for variations in laser output and temperature. These variations affect the amount of light emitted from the excited tags. Since the same laser beam split in beam splitter 12 is used to excite tags in exit stream 4 as well as in reference loop 7, this second measurement signal is used by the computer to normalize the measurements taken from exit stream 4. Other lasers such as Nd-YAG, for example, may be used.

Included in the detector is a two part data collection and analysis system. The first part comprises the components necessary to capture the exit stream signal and the reference loop signal. The second part, a computer, normalizes the exit stream signal with the reference signal, compares it with a computer model of system response with the appropriate tagged immunochemical and interprets it as a concentration of antigen in the input.

In order to exclude scattered laser light from the silicon photodiodes, the first part takes advantage of the long lifetime of the laser excited terbium emission. The nitrogen laser produces a 15 nS pulse of light. A box-car integrator 13 gates the response from the photodiodes so that the response is not recorded for approximately a microsecond after the start of the laser pulse. The box-car integrator 13 then continues to integrate the output of the photodiodes for approximately the next 100 microseconds. The output measured in this way from both the sample and reference systems is then ratioed and passed to the second part of the data analysis system, the computer.

As discussed above, the correlation of system output with the input concentration is complicated because antigens and antibodies are actually in a state of dynamic equilibrium as shown in equation (1). This means that even in a static assay system, antibody and antigen are constantly dissociating and reassociating. In the flow system presented here this would result in some of the tagged antibody constantly being swept into the detector even in the absence of sample antigen in the input. Further, this baseline will be constantly declining as more and more antibody is lost. Another factor to be considered is that when sample antigen is present, the increasing level of unconjugated tagged antigen will more effectively compete with the sample antigen for the free tagged antibody and will result in a decrease in the tagged antibody released for a given sample antigen input. Also, if flow through the reactor is essentially "slug flow" there will be no appreciable mixing of samples taken at different times. However, if a continuously stirred reactor, desirable for kinetic reasons, is used, the result is even more complex because of the statistical nature of the residence time of the sample antigen and the tagged antibody in the reactor.

The solution is to use a computer based system that:
1) contains a model of system response with tagged antibody contents, and
2) keeps track of the amount of tagged antibody lost during the course of the operation of the reactor.

Basically the system uses the actual measured tagged antibody level in the output and the integrated tagged antibody output since the initiation of reactor operation as indices to access a table giving corresponding input sample antigen levels. An alternative approach would use an appropriate regression model to convert the actual and integrated tagged antibody levels to the sample antigen concentration. The final result is reported using a suitable output device.

Figure 3:
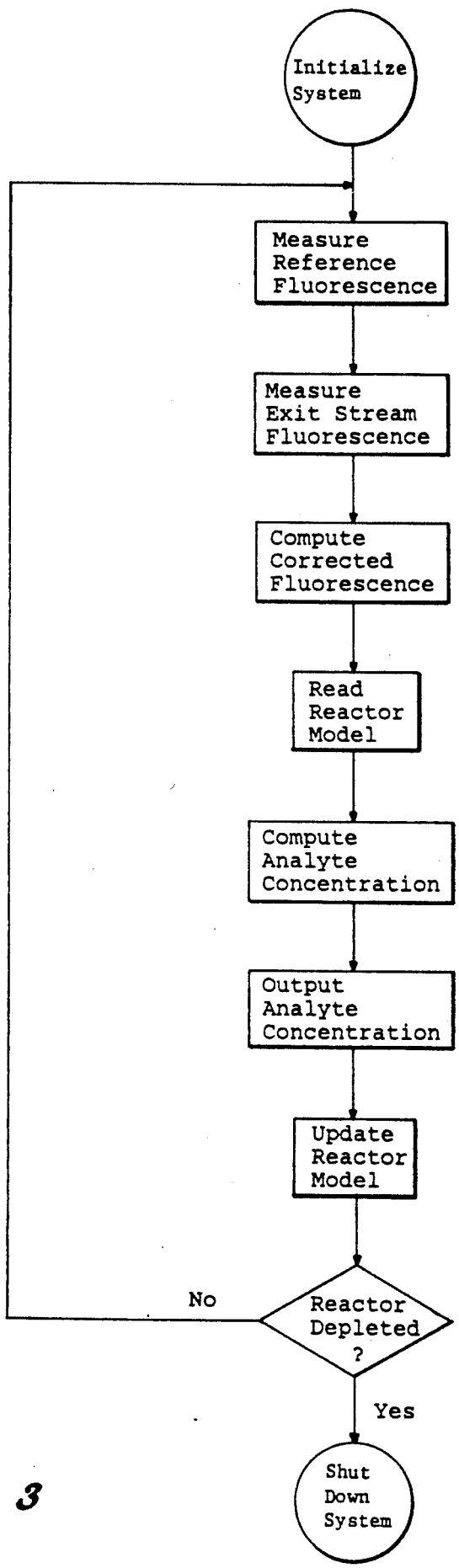
FIG. 3 is a flow chart of the computer software in the detection assembly.

FIG. 3 is a flow chart for software used in this computer based system. Although this particular software is designed for a system detecting fluorescent tags, the same software organization can be used where other type tags and other detecting techniques are used.

Furthermore, the detector presented in the dash line box of FIG. 2 may be configured with a lamp or a light emitting diode as light source. Other light sensors such as a phototransistor or a photomultiplier tube may be used.

The invention described is not intended to be limited to the embodiments disclosed but includes modifications made in the true spirit and scope of the invention.

What is claimed is:

1. A competitive binding reaction apparatus for the continuous detection and measurement of at least one analyte in an environment, said apparatus comprising:
   a sample collector assembly for capturing samples of the environment,
   a chemical reaction assembly,
   a detection asseembly, and
   means for continuously flowing the sample from the collector assembly to the reaction assembly and then to the detection assembly;
   wherein said chemical reaction assembly comprises:
      a first immunochemical immobilized on a surface; and
      a second immunochemical provided with tags and specifically bound to said first immunochemical, at least one of said first and second immunochemicals able to specifically bind to the analyte;
   wherein said detection assembly comprises:
      means for detecting said tags in an exit stream from said chemical reaction assembly and producing first signals representing the total amount of tagged immunochemical in the exit stream;
      a reference system comprising:
         a closed recirculating reference loop containing a known amount of said tagged second immunochemical,
         means for detecting tags in said reference loop and producing second signals;
         means for normalizing said first signals by comparing with said second signals;
      a model means of a response of said chemical reaction assembly to said tagged second immunochemical when there is no sample present as a function of time, said model means providing the amount of second tagged immunochemical in the exit stream as a function of time;
      means comparing said normalized first signals with said model means to adjust the total amount of tagged immunochemical by the amount of tagged second immunochemical and produce third signals representing the continuous detection and measurement of the analyte; and
   output means showing said third signals.

2. An apparatus according to claim 1, wherein the sample collector assembly comprises:
   means for capturing the sample from an environment,
   means for placing the sample in an aqueous solution, and
   means for conducting the resulting solution to the chemical reaction assembly.

3. An apparatus according to claim 1, wherein the chemical reaction assembly further comprises an aqueous compartment for enclosing said surface.

4. An apparatus according to claim 1, wherein said first immunochemical is an antibody specific to said analyte to be detected and measured and said second immunochemical is a tagged form of said analyte.

5. An apparatus according to claim 1, wherein said first immunochemical is a form of said analyte to be detected and measured and said second immunochemical is a tagged antibody specific to said analyte.

6. An apparatus according to claim 2, wherein said means conducting includes a pump.

7. An apparatus according to claim 1, wherein the tags are fluorescent and the means detecting comprises:
a light source for exciting the tags in the exit stream causing them to produce emissions; and
a light sensor detecting emissions produced by the fluorescent tags in the exit stream and producing said first signals.

8. An apparatus according to claim 7, wherein the reference system further comprises:
a beam splitter for splitting a beam from said light source into two parts, a first part exciting the tags in the exit stream and a second part exciting tags in the reference loop; and
a second light sensor detecting emissions produced by the fluorescent tags in said reference loop; and producing said second signals.

9. An apparatus according to claim 1, wherein the tags are one of cesium, barium or lithium, and the means detecting is a mass spectrometry means or an atomic absorption means.

10. An apparatus according to claim 1, wherein the tag is a substance not ordinarily present in the analyte or its environment.

11. An apparatus according to claim 1, wherein the surface is one of microspheres, a gel or an interior surface of the chemical reaction assembly.

12. An apparatus according to claim 7, wherein the light source is a laser and the light sensor is a photodiode.

13. A competitive binding reaction method for the continuous detection and measurement of at least one analyte in an environment, said method comprising:
continuously capturing samples of the environment in a sample collector assembly;
flowing said samples to a chemical reaction assembly;
contacting a surface in the chemical reaction assembly with said samples, said surface being provided with:
a first immunochemical immobilized thereon; and
a second immunochemical provided with detectable tags and specifically bound to said first immunochemical, one of said first and second immunochemicals able to specifically bind to said analyte;
flowing an exit stream from said chemical reaction assembly to a detection assembly;
detecting the presence of said tags in the exit stream from said chemical reaction assembly in said detection assembly and producing first signals representing the total amount of tagged immunochemical in the exit stream;
providing a closed recirculating reference system containing a known amount of said tagged second immunochemical;
detecting the presence of tags in said system and producing second signals;
normalizing said first signals by comparing with said second signals;
providing a model of the response of said chemical reaction assemble to said tagged second immunochemical when there is no sample present, as a function of time, said model providing the amount of tagged second immunochemical in the exit stream as a function of time;
comparing said normalized first signals with said model to adjust the total amount of tagged immunochemical by the amount of second tagged immunochemical and produce third signals representing the continuous detection and measurement of said analyte; and
displaying said third signals on an output device.

14. A method according to claim 13, comprising:
capturing the samples from the environment,
placing said samples in an aqueous solution, and
conducting the resulting solution to said surface.

15. A method according to claim 13, wherein the contacting step occurs within an aqueous compartment.

16. A method according to claim 13, wherein said first immunochemical is an antibody specific to said analyte to be detected and measured and said second immunochemical is a tagged form of said analyte.

17. A method according to claim 13, wherein said first immunochemical is a tagged antibody specific to said analyte.

18. A method according to claim 14, wherein the conducting step is performed with a pump.

19. A method according to claim 13, wherein the tag is fluorescent and the detecting step comprises:
applying a light beam to said tagged second immunochemical in the detection assembly to excite the tags in the exit stream and cause them to produce emissions; and
thereafter detecting emissions from the thus excited tags in the exit stream with a light sensor and producing said first signals.

20. A method according to claim 19, wherein the detecting step also includes:
applying a portion of said light beam to the known amount of tagged second immunochemical in said closed recirculating reference system to excite the tags and produce emissions; and
thereafter detecting the emissions from the thus excited tags in said reference system with a light sensor and producing third signals.

21. A method according to claim 13, wherein the tags are one of cesium, barium or lithium, and the detection assembly is a mass spectrometry means or an atomic absorption means.

22. A method according to claim 13, wherein the tag is a substance not ordinarily present in the analyte or its environment.

23. A method according to claim 13, wherein the surface is one of microspheres, a gel or an interior surface of the chemical reaction assembly.

24. A method according to claim 19, wherein the light beam is produced by a laser and the light sensor is a photodiode.

25. An apparatus according to claim 8, wherein the first, second and third signals are computer signals and wherein the means comparing is a computer.

26. A method according to claim 20, wherein the first, second and third signals are computer signals and wherein the means comparing step occurs within a computer.

* * * * *

UNITED STATES PATENT AND TRADEMARK OFFICE
CERTIFICATE OF CORRECTION

PATENT NO. : 5,045,479

DATED : September 3, 1991

INVENTOR(S) : Newman et al.

It is certified that error appears in the above—identified patent and that said Letters Patent is hereby corrected as shown below:

Title page, item (54):

Delete "Competetive" and substitute therefor -- Competitive --.

Column 4, line 45, after "laser" insert -- 1 --.

Signed and Sealed this

Second Day of March, 1993

Attest:

STEPHEN G. KUNIN

*Attesting Officer*

Acting Commissioner of Patents and Trademarks